(12) United States Patent
Lenker

(10) Patent No.: US 6,878,161 B2
(45) Date of Patent: Apr. 12, 2005

(54) STENT GRAFT LOADING AND DEPLOYMENT DEVICE AND METHOD

(75) Inventor: Jay A. Lenker, Laguna Beach, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 10/133,154

(22) Filed: Apr. 25, 2002

(65) Prior Publication Data

US 2002/0177890 A1 Nov. 28, 2002

Related U.S. Application Data

(63) Continuation-in-part of application No. 09/726,431, filed on Dec. 1, 2000, now Pat. No. 6,592,614, which is a division of application No. 09/030,719, filed on Feb. 25, 1998, now Pat. No. 6,176,875, which is a division of application No. 08/595,944, filed on Feb. 6, 1996, now Pat. No. 5,583,158, which is a continuation-in-part of application No. 08/583,814, filed on Jan. 5, 1996, now abandoned.

(51) Int. Cl.$^7$ ................................................ A61F 2/06
(52) U.S. Cl. ................... 623/1.13; 623/1.15; 623/1.32; 623/1.12
(58) Field of Search ........................ 623/1.13, 1.15, 623/1.49–1.53, 1.32, 1.12, 1.11, 1.16

(56) References Cited

U.S. PATENT DOCUMENTS

| | | | | |
|---|---|---|---|---|
| 6,165,210 A | * | 12/2000 | Lau et al. | 623/1.12 |
| 6,248,122 B1 | * | 6/2001 | Klumb et al. | 606/194 |
| 6,302,907 B1 | * | 10/2001 | Hijlkema | 623/1.16 |
| 6,309,411 B1 | * | 10/2001 | Lashinski et al. | 623/1.1 |
| 6,520,986 B2 | * | 2/2003 | Martin et al. | 623/1.13 |
| RE38,091 E | * | 4/2003 | Strecker | 623/1.12 |
| 6,551,350 B1 | * | 4/2003 | Thornton et al. | 623/1.13 |
| 6,676,698 B2 | * | 1/2004 | McGuckin et al. | 623/1.24 |
| 2003/0130721 A1 | * | 7/2003 | Martin et al. | 623/1.13 |

* cited by examiner

*Primary Examiner*—David H. Willse
*Assistant Examiner*—Suzette J. Gherbi

(57) ABSTRACT

An endoluminal prosthesis includes a tubular graft, an expandable annular support structure and a restraining mechanism restraining the prosthesis in a collapsed configuration in which the annular support structure is compressed to a low profile. The restraining mechanism holds the annular support structures in the collapsed configuration until the prosthesis is positioned for deployment. The restraining mechanism is then released to allow the annular support structures to expand into conforming engagement with the inner wall of a lumen in which the prosthesis is to be deployed. A feature according to the invention provides a balloon catheter onto which the prosthesis is loaded for deployment where the balloon is expanded to provide a radial force to release the restraining mechanism. Another feature provides for a restraining member that breaks upon application of the radial force to release the annular support structure from its constrained configuration. Another feature of the invention provides for independent and/or sequential release of the annular support members. Various types of annular support members attached to tubular grafts in a variety of manners may be used in accordance with the invention. The invention may be used in tubular grafts for endoluminal placement within a body lumen, including blood vessels, and for the treatment of abdominal and other aneurysms.

42 Claims, 16 Drawing Sheets

STENT GRAFT LOADING AND DEPLOYMENT DEVICE AND METHOD

RELATED APPLICATIONS

This application is a continuation-in-part of U.S. patent application Ser. No. 09/726,431 filed on Dec. 1, 2000 now U.S. Pat. No. 6,592,614, which is a divisional of U.S. application Ser. No. 09/030,719, filed on Feb. 25, 1998, now U.S. Pat. No. 6,176,875, which is a divisional of U.S. application Ser. No. 08/595,944 filed on Feb. 6, 1996, now U.S. Pat. No. 5,583,158, which is a continuation-in-part of U.S. application Ser. No. 08/583,814 filed on Jan. 5, 1996 now abandoned.

FIELD OF THE INVENTION

The present invention relates to tubular prostheses such as grafts and endoluminal prostheses including, for example, stent-grafts and aneurysm exclusion devices, and methods for placement of such grafts and endoluminal structures. Further, the present invention relates to a stent graft deployment device and method.

BACKGROUND OF THE INVENTION

A wide range of medical treatments have been previously developed using "endoluminal prostheses," which terms are herein intended to mean medical devices which are adapted for temporary or permanent implantation within a body lumen, including both naturally occurring or artificially made lumens. Examples of lumens in which endoluminal prostheses may be implanted include, without limitation: arteries such as those located within coronary, mesentery, peripheral, or cerebral vasculature; veins; gastrointestinal tract; biliary tract; urethra; trachea; hepatic shunts; and fallopian tubes. Various types of endoluminal prostheses have also been developed, each providing a uniquely beneficial structure to modify the mechanics of the targeted luminal wall.

A number of vascular devices have been developed for replacing, supplementing or excluding portions of blood vessels. These vascular grafts may include but are not limited to endoluminal vascular prostheses and stent grafts, for example, aneurysm exclusion devices such as abdominal aortic aneurysm ("AAA") devices that are used to exclude aneurysms and provide a prosthetic lumen for the flow of blood.

One very significant use for endoluminal or vascular prostheses is in treating aneurysms. Vascular aneurysms are the result of abnormal dilation of a blood vessel, usually resulting from disease or a genetic predisposition, which can weaken the arterial wall and allow it to expand. While aneurysms can occur in any blood vessel, most occur in the aorta and peripheral arteries, with the majority of aneurysms occurring in the abdominal aorta. Typically an abdominal aneurysm will begin below the renal arteries and may extend into one or both of the iliac arteries.

Aneurysms, especially abdominal aortic aneurysms, have been treated in open surgery procedures where the diseased vessel segment is bypassed and repaired with an artificial vascular graft. While considered to be an effective surgical technique in view of the alternative of a fatal ruptured abdominal aortic aneurysm, the open surgical technique suffers from a number of disadvantages. The surgical procedure is complex and requires long hospital stays due to serious complications and long recovery times and has high mortality rates. In order to reduce the mortality rates, complications and duration of hospital stays, less invasive devices and techniques have been developed. The improved devices include tubular prostheses that provide a lumen or lumens for blood flow while excluding blood flow to the aneurysm site. They are introduced into the blood vessel using a catheter in a less or minimally invasive technique. Although frequently referred to as stent-grafts, these devices differ from covered stents in that they are not used to mechanically prop open natural blood vessels. Rather, they are used to secure an artificial lumen in a sealing engagement with the vessel wall without further opening the natural blood vessel that is already abnormally dilated.

Typically these endoluminal prostheses or stent grafts are constructed of graft materials such as woven polymer materials (e.g., Dacron,) or polytetrafluoroethylene ("PTFE") and a support structure. The stent-grafts typically have graft material secured onto the inner diameter or outer diameter of a support structure that supports the graft material and/or holds it in place against a luminal wall. The prostheses are typically secured to a vessel wall above and below the aneurysm site with at least one attached expandable annular spring member that provides sufficient radial force so that the prosthesis engages the inner lumen wall of the body lumen to seal the prosthetic lumen from the aneurysm. In some devices, a radially expandable member partially extends proximally of the graft material providing openings through which blood may flow to prevent blockage when placed at or near the junction of other vasculature (e.g., at or near the renal artery where a stent graft is being used to exclude an abdominal aortic aneurysm). In other devices, other mechanisms have also been used to engage the vessel walls such as, for example, forcibly expandable members or hook like members that puncture the vessel wall. In some devices where attached expandable ring members are used, a support bar attaches to two or more of the ring members to provide columnar support along the length of the bar.

Vessels with aneurysms and other structural abnormalities to be treated with endoluminal prostheses, and their associated vessels such as branch vessels, frequently have tortuous and twisted anatomies. One challenge in implanting the endoluminal prostheses is to provide delivery catheter access to the site. In particular, the delivery catheter and device frequently require maneuvering through the tortuous or narrowed diseased vessels while avoiding kinking, crimping, folding or collapse of the catheter or stent. It would therefore be desirable to provide a stent graft and delivery system with a relatively low profile or a relatively small diameter for maneuvering through narrowed or tortuous vessels. It would further be desirable to provide such a flexible endoluminal tubular graft and delivery system that reduces kinking crimping, folding and collapse when placed through tortuous, twisted vessels.

SUMMARY OF THE INVENTION

An embodiment according to present invention provides an improved endoluminal prosthesis having a tubular graft with a support structure attached to the tubular graft, configured in a manner that provides device flexibility while maintaining a relatively small pre-deployed, collapsed profile.

An embodiment of the endoluminal prosthesis comprises a tubular member constructed of a graft material and at least one annular support member. The tubular graft is formed of a woven fiber for conducting fluid. The tubular member includes, a proximal opening and a distal opening providing a lumen through which body fluids may flow. When deployed annular support members support the tubular graft and/or maintain the lumen in a conformed, sealing arrangement with the inner wall of a body lumen.

The annular support members each comprise an annular expandable member formed by a series of connected compressible diamond structures. Alternatively, the expandable member may be formed of an undulating or sinusoidal patterned wire ring or other compressible spring member. Preferably the annular support members are radially compressible springs biased in a radially outward direction, which when released, bias the prosthesis into conforming fixed engagement with an interior surface of the vessel. Annular support members are used to create a seal between the prosthesis and the inner wall of a body lumen as well as to support the tubular graft structure. The annular springs are preferably constructed of Nitinol. Examples of such annular support structures are described, for example, in U.S. Pat. Nos. 5,713,917 and 5,824,041 incorporated herein by reference. When used in an aneurysm exclusion device, the support structures have sufficient radial spring force and flexibility to conformingly engage the prosthesis with the body lumen inner wall, to avoid excessive leakage, and prevent pressurization of the aneurysm, i.e., to provide a leak resistant seal. Although some leakage of blood or other body fluid may occur into the aneurysm isolated by the prosthesis, an optimal seal will reduce the chances of aneurysm pressurization and resulting rupture.

The annular support members are attached or mechanically coupled to the graft material along the tubular graft by various means, such as, for example, by stitching onto either the inside or outside of the tubular graft.

A feature according to the invention provides restraining members that hold the annular springs in a compressed configuration until the prosthesis is positioned and the restraining members are released. The restraining members permit deployment of the prosthesis without the use of a retaining sheath on the catheter. A highly flexible sheath may be used with the catheter to prevent catching of the prosthesis on the inner lumen wall during delivery to the deployment site. Such sheath may be constructed of a thin, highly flexible material that does not require radially retaining strength to retain the annular springs. Once the prosthesis is placed at the deployment site, the restraining members are released by one of several mechanisms. In one embodiment, the restraining mechanisms are broken or released by inflation of a balloon over which the compressed and restrained prosthesis is placed. Such restraining mechanisms may comprise, for example, a suture, clip or other mechanism holding all or a portion of the annular member in the compressed, collapsed configuration. The restraining mechanism may comprise a member encircling the entire ring such as a suture, wire, thread, or a band of material. Alternatively an expandable cover may be placed over several or all of the compressed annular support structures. Breaking or releasing the restraining member permits the self-expanding annular support structure to expand the prosthesis into conforming engagement with the inner wall of the lumen. Alternative mechanisms may be used to release the restraining mechanisms. For example, a thread loop tied around a support structure may be released by actuating or pulling on a thread to untie the loop. In one embodiment, the restraining mechanisms on each of the annular support structures may be individually released so that if desired, the annular support structures can be released in a desired sequence.

An embodiment according to the present invention provides such a tubular graft and improved support structure for endoluminal placement within a blood vessel for the treatment of abdominal and other aneurysms. In this embodiment, the endoluminal prosthesis is an aneurysm exclusion device forming a lumen for the flow of body fluids excluding the flow at the aneurysm site. The aneurysm exclusion device may be used for example, to exclude an aneurysm in the aorta, such as in the abdominal aorta or in the thoracic region. In an abdominal aorta, the prosthesis may be bifurcated.

In an embodiment of an Abdominal Aortic Aneurysm ("AAA") device, the prosthesis provides sealing attachment of the annular support structure to the inner wall of the body lumen.

The endoluminal prosthesis may be in the form of either a straight single-limb tubular member or a generally Y-shaped bifurcated tubular member having a trunk joining at a graft junction with a pair of lateral limbs, namely an ipsilateral limb and a contralateral limb. In a bifurcated prosthesis, the proximal portion of the prosthesis comprises a trunk with a proximal opening and the distal portion is branched into at least two branches with distal openings. Thus body fluids may flow from the proximal opening through the distal openings of the branches. Preferably the ipsilateral limb is longer so that when deployed, it extends into the common iliac. A single limb extension member is provided having a mating portion for coupling with a lateral limb of a bifurcated member and an adjustable length portion extending coaxially from a distal end of the mating portion.

The compressed profile of the prosthesis is sufficiently low to allow the endoluminal graft to be placed into the vasculature using a low profile delivery catheter. The prosthesis can be placed within a diseased vessel via deployment means at the location of an aneurysm. Various means for deliver of the device through the vasculature to the site for deployment, are well known in the art and may be found for example is U.S. Pat. Nos. 5,713,917 and 5,824,041. In general, the endoluminal prosthesis is radially compressed and restrained by a restraining mechanism and loaded on or may otherwise be coupled to, the distal end of the catheter for delivery to the deployment site. The aneurysm site is located using an imaging technique such as fluoroscopy and is guided through a femoral iliac artery with the use of a guide wire to the aneurysm site. Once appropriately located, any protective sheath covering the tubular graft may be retracted. The annular support member restraining mechanism or mechanisms are then released, thus allowing the annular springs to expand and attach or engage the tubular member to the inner wall of the body lumen. The iliac extension is also loaded into a catheter and is then located into the main body of the stent graft and within the iliac vessel where it is deployed. When deployed, the iliac extension is engaged using annular springs proximally within the inner lumen of the main body and distally with the inner wall of the iliac vessel.

These and further aspects of the invention are exemplified and in the detailed description of embodiments according to the invention described below.

DETAILED DESCRIPTION

FIGS. 1A–8 illustrate various embodiments of the endoluminal prosthesis, delivery systems and methods according to the present invention. Although an endoluminal prosthesis, delivery system and method according to the invention may be used in any body lumen that conducts body fluid, they are described herein with reference to treatment of an aortic aneurysm, in particular in the abdomen of a patient.

Figure 1A:
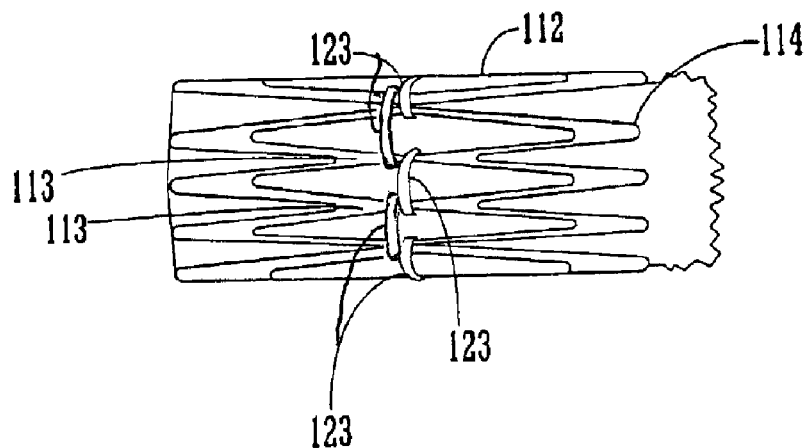
FIG. 1A is a side elevational view of an endoluminal prosthesis according to an embodiment of the invention in a first, constrained configuration.
Figure 1B:
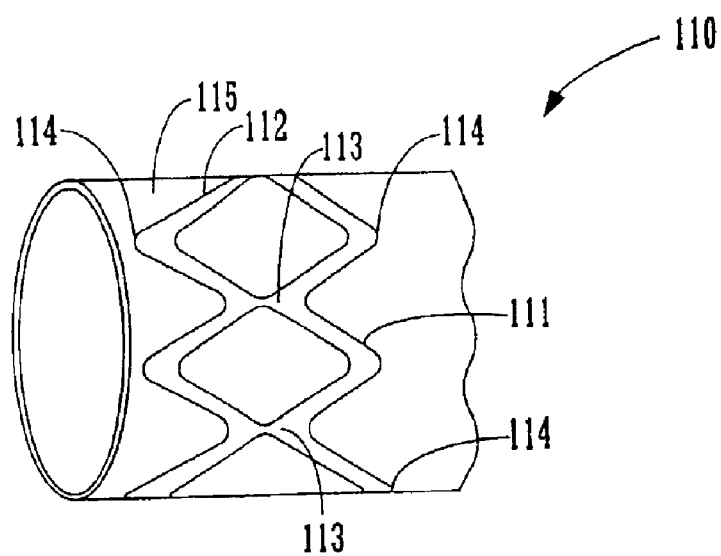
FIG. 1B is a side elevational view of the endoluminal prosthesis of FIG. 1A in a second, released configuration.

FIGS. 1A and 1B illustrate an embodiment of an endoluminal prosthesis 110. The prosthesis 110 comprises a tubular graft 115 and a series of radially compressible annular support members 112 attached to tubular graft 115. The annular support members 112 support the graft and/or bias the prosthesis 110 into conforming fixed engagement with an interior surface of an aorta 10 (See FIG. 2C). The annular support members 112 are preferably spring members having a predetermined radii and are preferably constructed of a material such as Nitinol in a superelastic, shape set, annealed condition The tubular graft 115 is preferably formed of a biocompatible, low-porosity woven fabric, such as a woven polyester. The graft material is thin-walled so that it may be compressed into a small diameter, yet is capable of acting as a strong, leak-resistant fluid conduit when expanded to a cylindrical tubular form. In this embodiment, the annular support members 112 are sewn on to the outside of the tubular graft 115 material by sutures. Alternative mechanisms of attachment may be used (such as embedding or winding within material, adhesives, staples or other mechanical connectors) and the annular support members 112 may be attached to the inside of the tubular graft 115. The support members 112 comprise a series of connected diamond structures 111 around the circumference of the annular member 112 that form peaks and valleys 114.

As illustrated in FIG. 1A, the prosthesis 110 is in a collapsed configuration. The diamond shaped structures 111 are flattened or compressed by drawing the middle portions 113 of each of two adjacent diamond-shaped structure joints together with a restraining mechanism 123. The restraining mechanism 123 may be a suture or clip that will break or release upon application of radially expanding force from inside the prosthesis 110. As illustrated in FIG. 1A, a restraining mechanism 123 is placed about the middle portion of two joints of the diamond structures 111 to draw the corresponding diamond shaped structures 111 into a compressed configuration. A restraining mechanism 123 may be used to compress one or more diamond structures 111. FIG. 1B illustrates the prosthesis 110 in an expanded configuration after the restraining mechanisms 123 have been released.

Figure 2A:
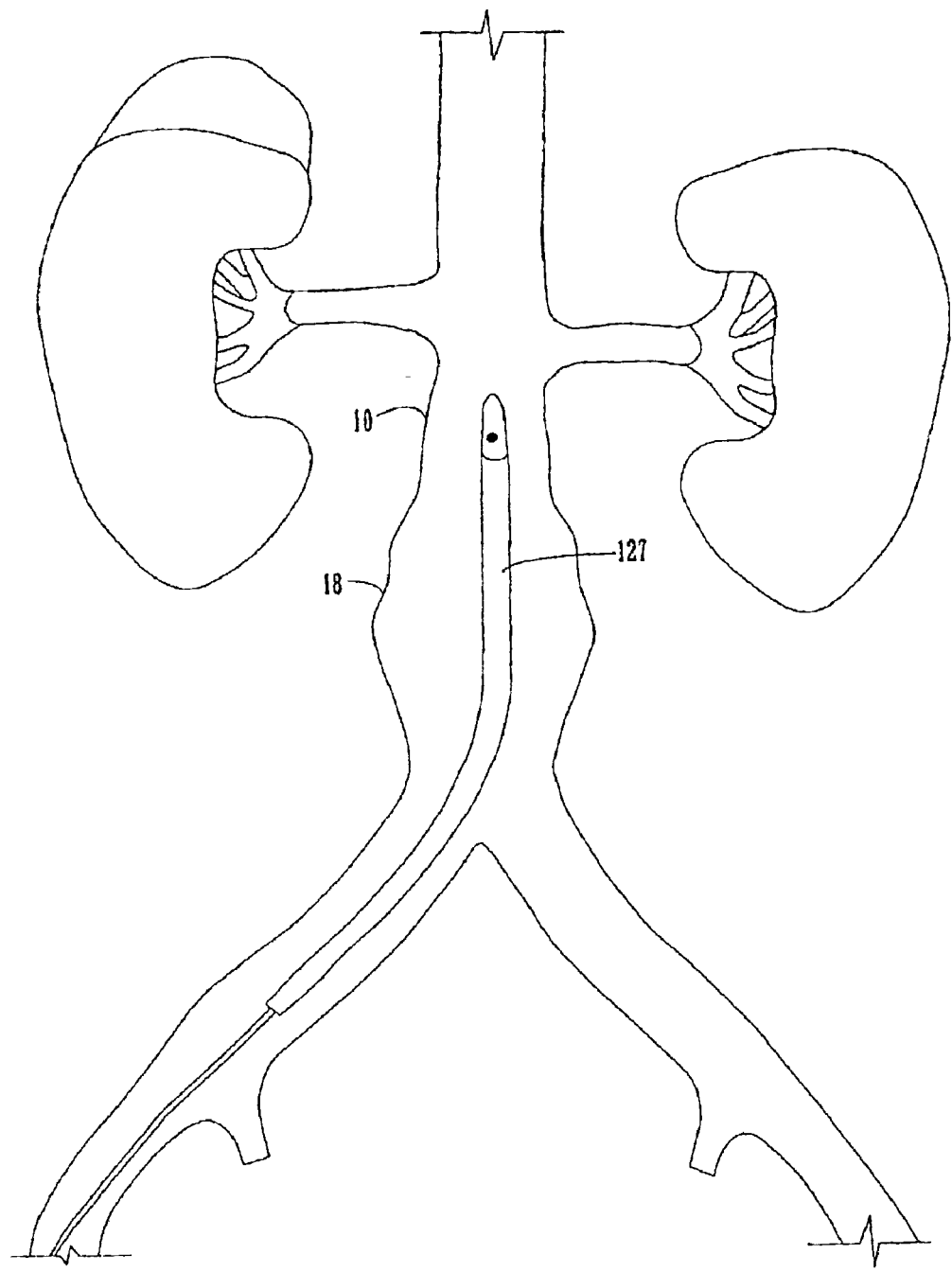
FIG. 2A is a side elevational partial cross sectional view of the endoluminal prosthesis of FIG. 1A and delivery system as the prosthesis is positioned within the vasculature.
Figure 2B:
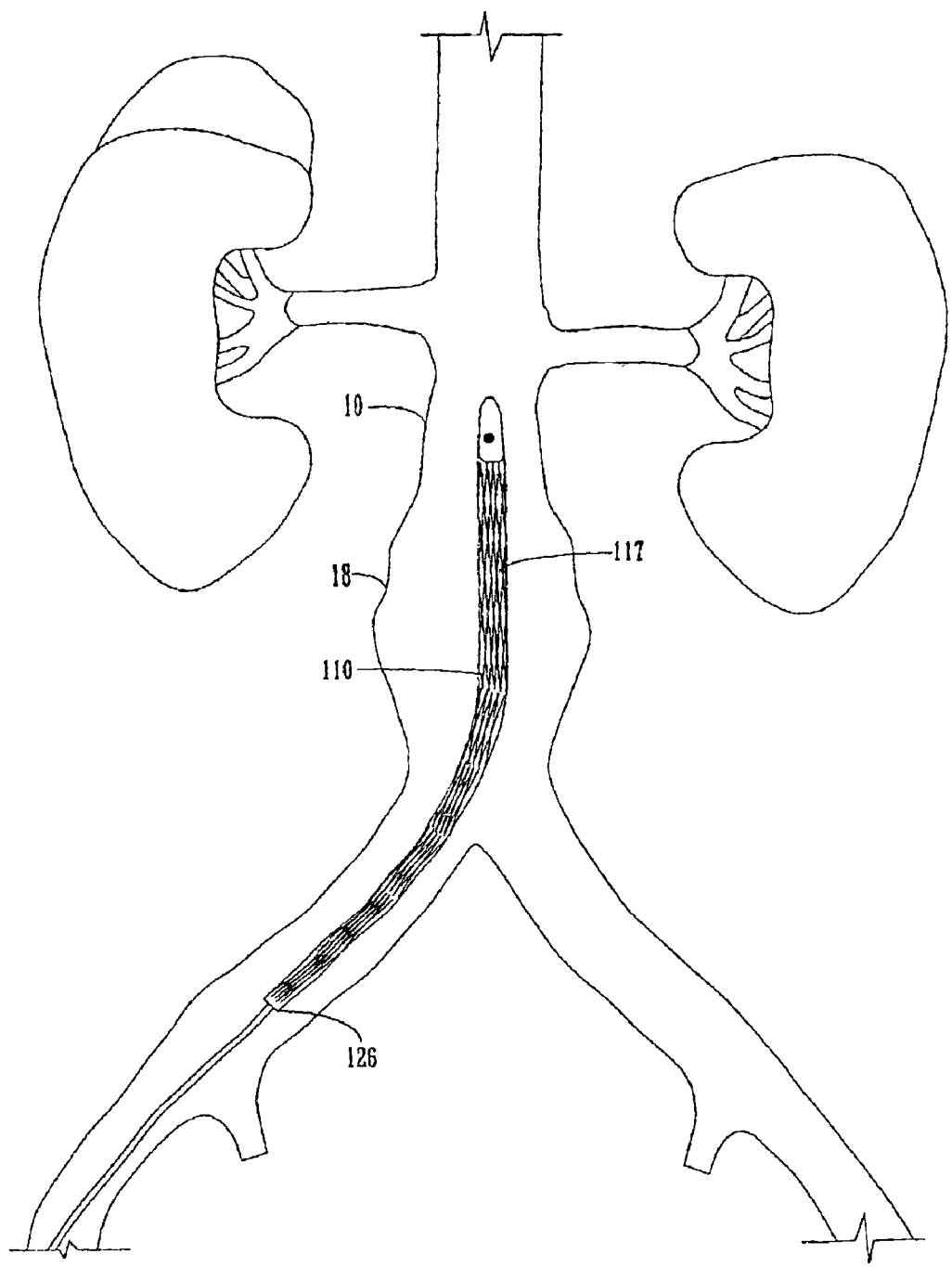
FIG. 2B is a side elevational partial cross sectional view of the endoluminal prosthesis of FIG. 1A and delivery system after the graft cover is retracted.
Figure 2C:
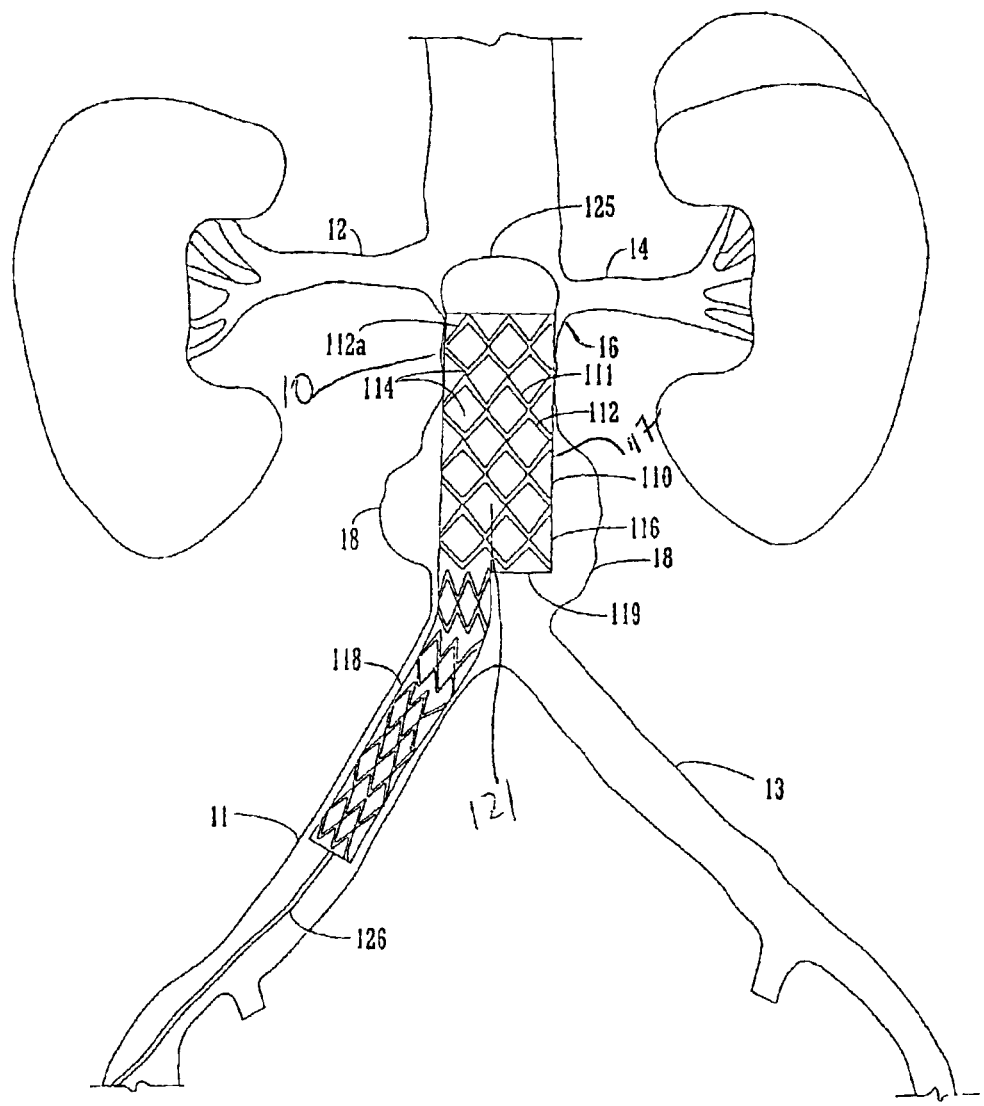
FIG. 2C is a side elevational partial cross sectional view of the endoluminal prosthesis of FIG. 1A and delivery system as the prosthesis is deployed within the vasculature.

Referring to FIG. 2C, the prosthesis 110 includes a main body portion 116 and a contralateral iliac extension limb (not shown). The main body portion 116 is a tubular bifurcated member having an aortic portion 117, a long ipsalateral iliac limb portion 118, and a short iliac portion 119. In FIG. 2C, prosthesis 110 is shown in place in an abdominal aorta 10. The aorta 10 is joined by renal arteries 12 and 14 at the aorto-renal junction 16. Just below the aorta-renal junction 16 is an aneurysm 18, a diseased region where the vessel wall is weakened and expanded. Below the aneurysm 18, the aorta 10 bifurcates into right and left iliac vessels 11, 13, respectively. The elongated bifurcated tubular prosthesis 110 is deployed at the region of aneurysm 18 for the purpose of relieving blood pressure against the weakened vessel wall, by acting as a fluid conduit through the region of the aneurysm 18. In its deployed configuration, prosthesis 110 defines a conduit of blood flow through the aorta 10. Annular support members 112 are designed to exert a radially outward force sufficient to bias the tubular graft 115 of the endoluminal prosthesis 110 into conforming fixed engagement with the interior surface of aorta 10 above aneurysm 18, to support the tubular graft 115, and/or to provide a leak resistant seal between the prosthesis and the inner wall of the aorta 10. The proximal aortic portion 117 of the prosthesis 110 is located within aorta 10, and the long ipsalateral iliac portion limb 118 is located within the right iliac vessel 11. After deployment of the main body portion 116, the contralateral iliac extension limb (not shown) is located within left iliac vessel 13, and near the graft junction 121 within the short iliac portion 119.

To deploy the prosthesis 110, the main body portion 116 of the prosthesis 110 may be loaded into a catheter 126. The prosthesis 110 is placed in a collapsed configuration over a balloon 125 of the catheter 126. Annular support members 112 are held in a radially compressed configuration by the restraining mechanisms 123 to facilitate delivery of the prosthesis 110. A thin flexible sheath or cover 127 is placed over the prosthesis 110 to prevent it from damaging or catching on the luminal wall as it is delivered to the aneurysm site. Restraining of the prosthesis by the cover 127 is minimal so that when it is retracted, the prosthesis 110 remains in the collapsed configuration. The main body portion 116 is delivered in a compressed state via catheter 126 through a surgically accessed femoral artery, to the desired deployment site. (FIG. 2A) When the distal end of the catheter 126 is located at the deployment site the cover 127 is retracted (FIG. 2B) in a manner not shown but, for example, by retracting a sheath as is well understood by persons skilled in the art. The balloon 125 is inflated (FIG. 2C) to open the tubular graft 115 and support members 112 and break or release the restraining mechanisms 123 that were holding the annular members 112 in the compressed configuration. The annular support members 112 released from the restraint of the restraining mechanisms 123, then expand or are expanded into the deployed position illustrated in FIG. 2C.

Using a second catheter, the contralateral iliac extension limb may be separately deployed through a surgically accessed femoral artery after placement of the main body portion 116. This is not shown here but is well understood by persons skilled in the art.

Surgical methods and apparatus for accessing the surgical site are generally known in the art and may be used to place the catheter within the vasculature and deliver the prosthesis to the deployment site. Additionally, various actuation mechanisms for retracting sheaths and inflating balloons of balloon catheters are known in the art. The prosthesis may be delivered to the deployment site by one of several ways. A surgical cut down may be made to access a femoral iliac artery. The catheter is then inserted into the artery and guided to the aneurysm site using fluoroscopic imaging where the device is then deployed. The annular support members supporting the graft, biased in a radially outward direction, are released to expand and engage the prosthesis in the vessel against the vessel wall to provide an artificial lumen for the flow of blood. Another technique includes percutaneously accessing the blood vessel for catheter delivery, i.e., without a surgical cutdown. An example of such a technique is set forth in U.S. Pat. No. 5,713,917, incorporated herein by reference.

Figure 3A:
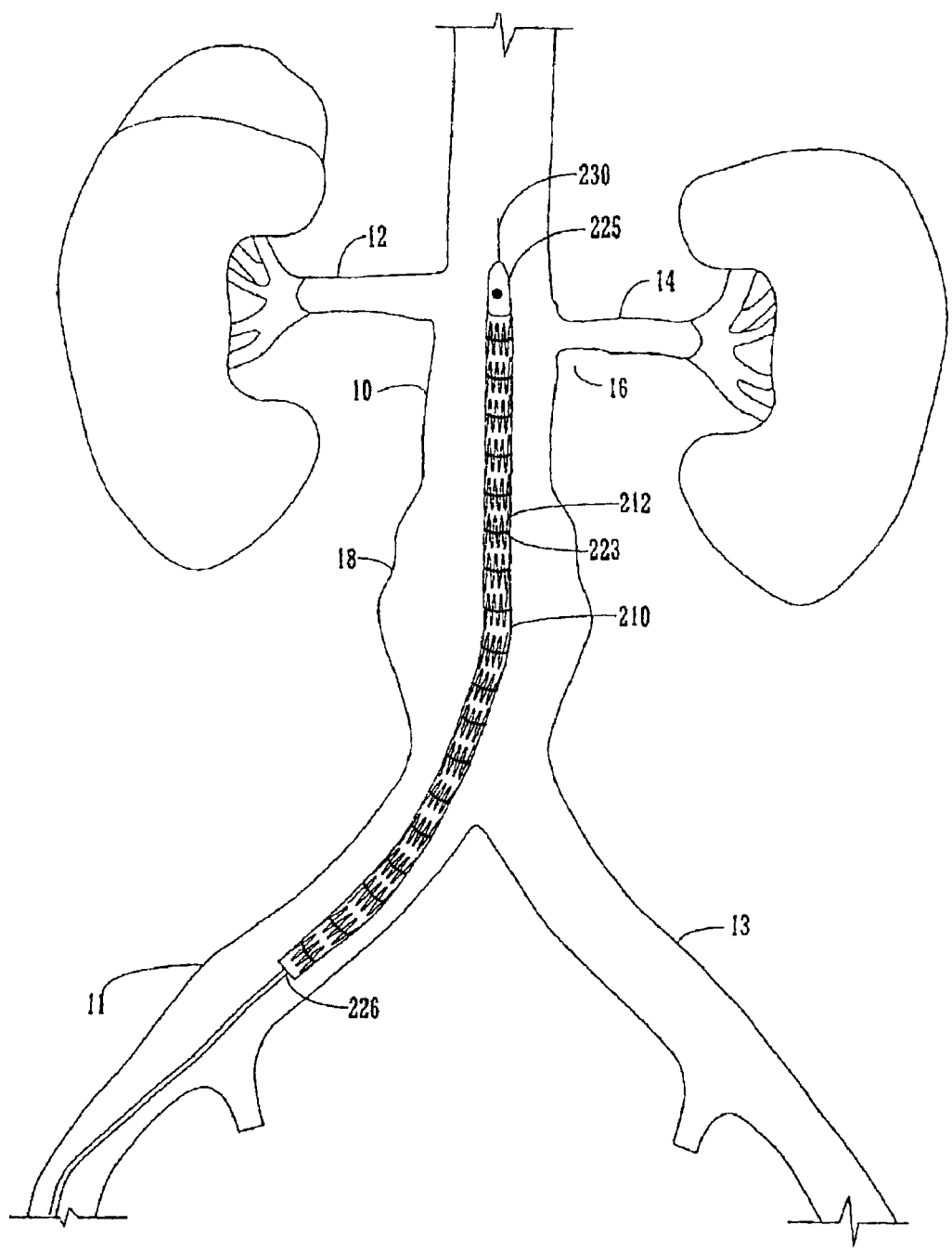
FIG. 3A is a side elevational view of another embodiment of an endoluminal prosthesis and delivery system with the prosthesis loaded on a delivery catheter and placed in position for deployment according to the invention.
Figure 3B:
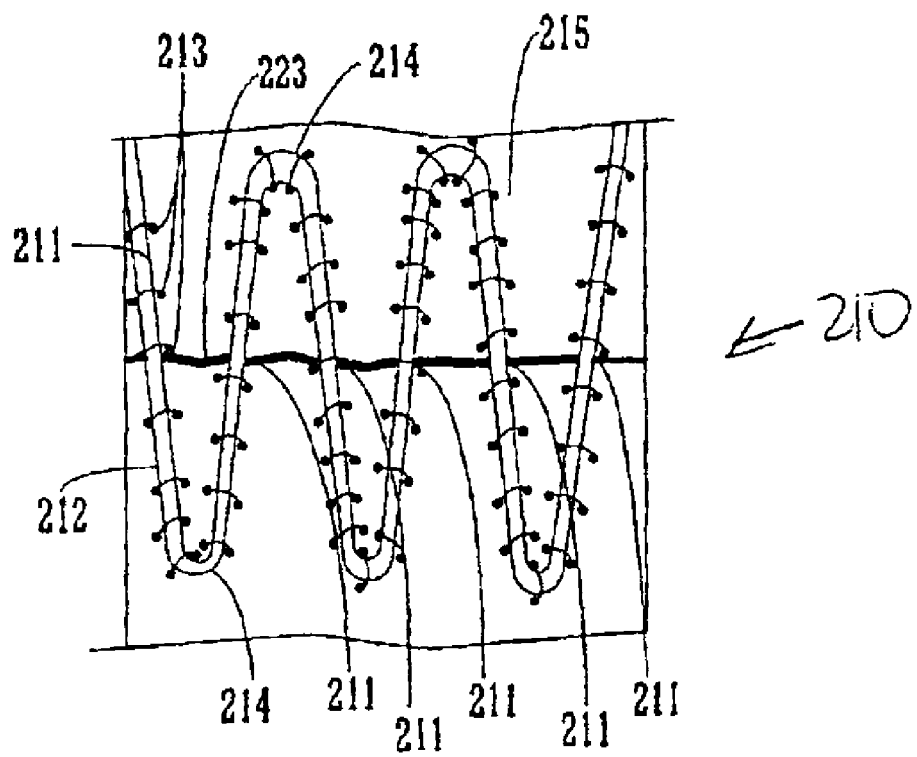
FIG. 3B is an enlarged view of an annular member sewn on the tubular graft of the prosthesis of FIG. 3A.
Figure 3C:
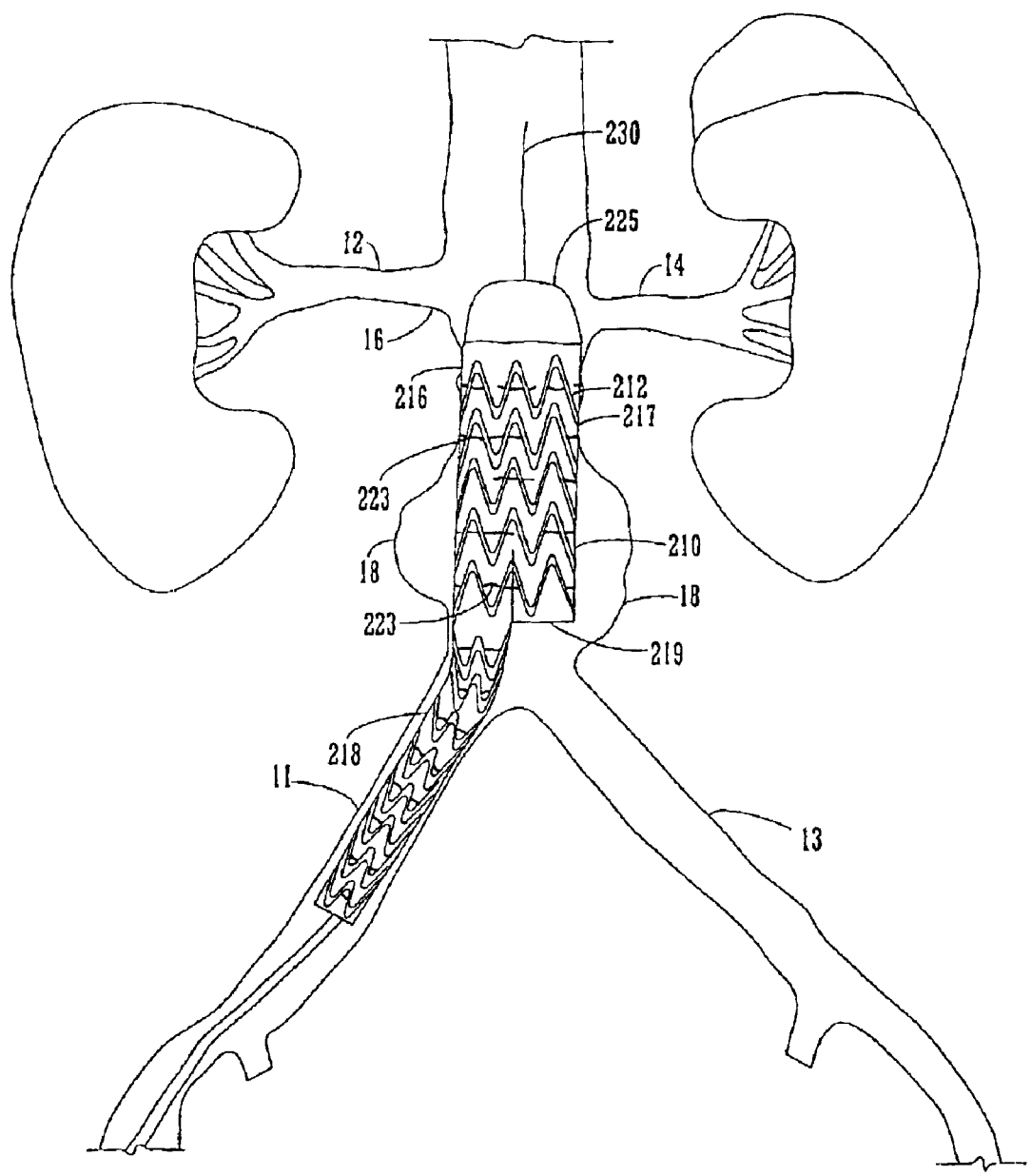
FIG. 3C is a side elevational partial cross-section of the endoluminal prosthesis and delivery system of FIG. 3A after the prosthesis is deployed.

FIGS. 3A–3C illustrate another embodiment of the prosthesis and delivery system according to the invention. The prosthesis 210 comprises a plurality of annular members 212 attached to the outside of a tubular graft member 215. The prosthesis 210 includes a main body portion 216 and a contralateral iliac extension limb (not shown). The main body portion 216 is a tubular bifurcated member having an aortic portion 217, a long ipsalateral iliac limb portion 218, and a short iliac portion 219. The prosthesis 210 is constructed of similar materials as the prosthesis 110 described above. The support members 212 comprise a series of struts 211 connected by curved portions 214 forming peaks and valleys around the circumference of the annular member 212. Alternatively the annular members 212 may be other ring structures, such as, for example, connected diamond structures. The annular support members 212 are sewn on to the outside of the tubular graft 215 with sutures 213. Alternative mechanisms of attachment may be used and the annular support members 212 may be attached to the inside of the tubular graft 215.

As illustrated in FIGS. 3A and 3B, the prosthesis 210 is loaded over an expandable balloon 225 on the distal end of a delivery catheter 226. The annular support members 212 are held into a compressed configuration by a series of failure fibers or sutures 223 that are placed around the tubular graft 215 in positions that encircle the annular support members 212 within the circumference of the support members 212. The sutures 223 have sufficient strength to hold the graft 215 of the prosthesis 210 together while the sutures 213 connect the compressed annular support 212 to the tubular graft 215. Thus the annular support members 212 are held in place such that the failure sutures 223 hold the compressed configuration. The failure sutures 223 have failure properties that stretch and or break the sutures 223 when sufficient radial expansion force is applied, i.e., by the expansion of the balloon 225 of the delivery catheter 226. The sutures 223 may for example be a suture material, other fiber, wire or other member selected to fail, break or expand upon application of the radial force by a radially expanding or extending member. The sutures may be constructed e.g. of Polyviolene 5-0 Braided Coated Polyester or Polyviolene 6-0 Braided Coated Polyester, both manufactured by Surgical Specialties Corporation in Reading, Pa. 19607. The sutures 223 as illustrated are initially sewn through the graft material and are knotted to anchor the sutures 223 to the graft 215. Each suture 223 is then wrapped around the tubular graft 215, thus encircling the inner circumference of the annular support members 112, holding the graft 215 together while the graft 215 through the sutures 213 holds the annular support members 212 in a compressed configuration. Alternatively, the sutures 223 may be wrapped around the annular support member or may alternate in some manner, over and under the support members. In such instance, the suture 223 may be place through knots in the sutures 213 to prevent slipping off of the annular support members 212.

As illustrated in FIG. 3A, the prosthesis is placed by initially inserting a guide wire 230, through an iliac vessel 11 into the aorta 10, above the aorta renal junction 16. The loaded delivery catheter 226 is placed over the guidewire 230, which helps guide the catheter 226 to the aneurysm site 18. The catheter 226 is placed using generally known imaging techniques, in position below the aorta renal junction 16 and within the aneurysm 18.

As illustrated in FIG. 3C, the balloon 225 (which may extend from the proximal to distal end of the prosthesis or within a portion thereof) is inflated and the force of expansion breaks the sutures 223 releasing the annular support members 212 which then expand to engage the inner wall of the aorta 10. The prosthesis 210 illustrated in FIG. 3C is deployed in the aorta with the proximal aortic portion 217 of the prosthesis 210 located within aorta 10, and the long ipsalateral iliac portion limb 218 located within the right iliac vessel 11. A contralateral limb may subsequently be deployed in a similar manner in which a portion of the contralateral limb is placed within the short iliac limb portion 219 of the main body portion 216.

Referring now to FIGS. 4A–4B and FIGS. 5A–5D, another embodiment according to the invention is illustrated. A prosthesis 310 is in a compressed configuration in FIG. 4A and in an expanded configuration in FIG. 4B. The prosthesis 310 comprises a plurality of annular support members 312 attached to the outside of a tubular graft member 315. The prosthesis 310 includes a main body portion 316 and a contralateral iliac extension limb (not shown). The main body portion 316 is a tubular bifurcated member having an aortic portion 317, a long ipsalateral iliac limb portion 318, and a short iliac portion 319. The prosthesis 310 is constructed of similar materials as the prosthesis 310. The support members 312 comprise a series of connected diamond structures 311 around the circumference of the annular member 312 that form peaks and valleys 314. Alternatively, the support members may comprise a series of struts connected by curved portions forming peaks and valleys around the circumference of the annular member. The annular support members 312 are sewn on to the outside of the tubular graft 315 with sutures. Alternative mechanisms of attachment may be used (such as embedding or winding within material, adhesives, staples or other mechanical connectors) and the annular support members 312 may be attached to the inside of the tubular graft 315.

Each of the annular support members 312 are tied closed (in a compressed configuration) with a restraining member 323 around its circumference. The restraining member 323 may be a thread, suture, wire or the like. The release of each restraining member is separately actuable. In the embodiment illustrated, a single thread or wire corresponding to each annular support member 312 is actuated by pulling on an actuating thread 324 of the release mechanism 323 corresponding to the annular support member 312. Accordingly, the annular support members 312 may be deployed in any desired sequence.

Figure 4A:
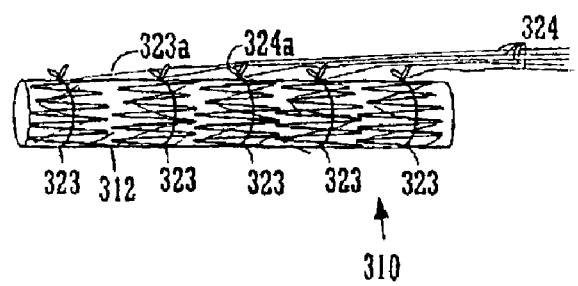
FIG. 4A is a side elevational view of another embodiment of an endoluminal prosthesis according to a delivery system of the invention in a first, constrained configuration.
Figure 4B:
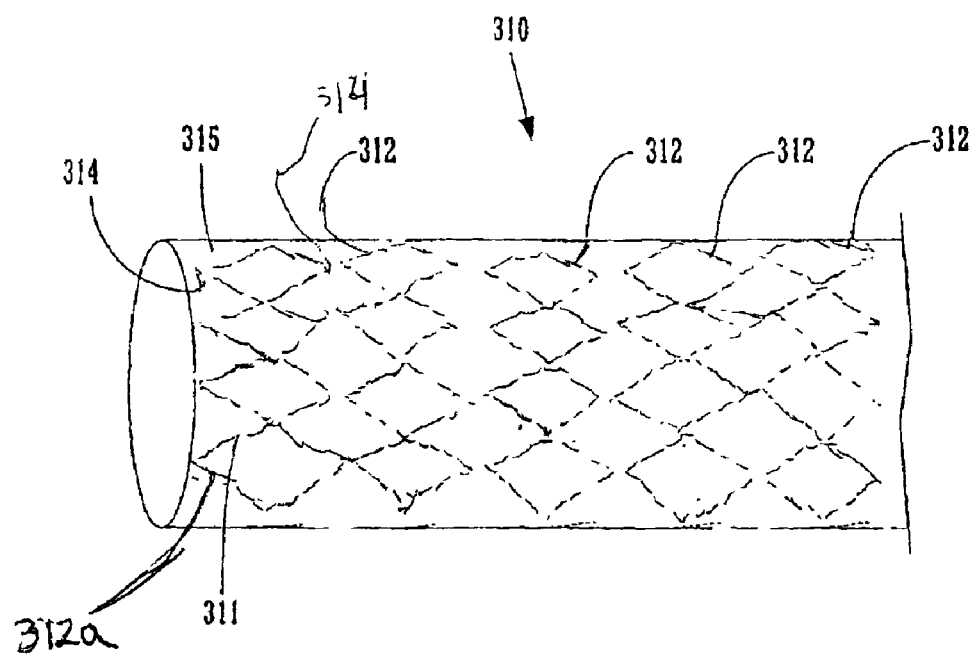
FIG. 4B is a side elevational view of the endoluminal prosthesis of FIG. 4A in a second, open configuration.
Figure 5A:
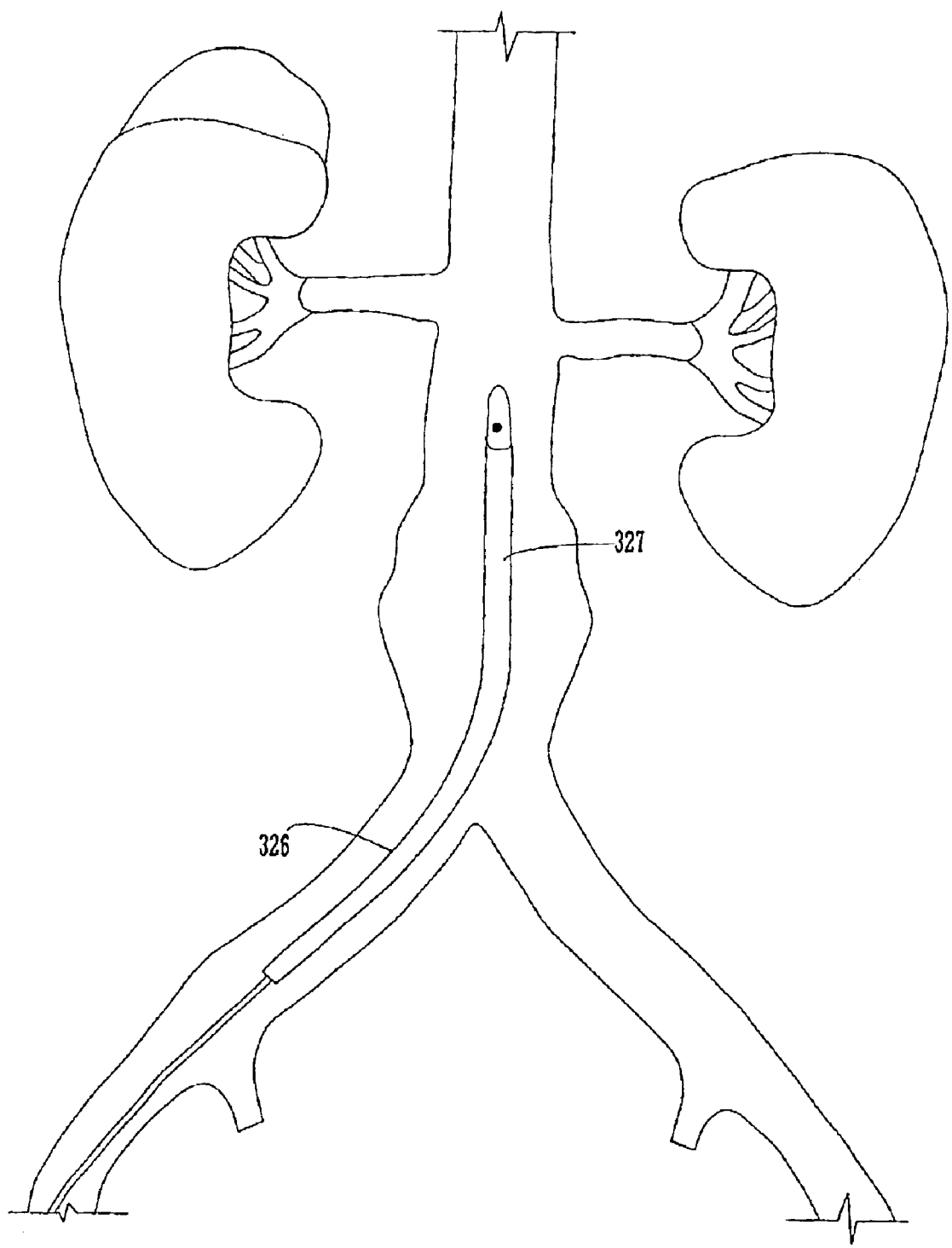
FIG. 5A is a side elevational partial cross sectional view of the endoluminal prosthesis and delivery system of FIG. 4A as it is positioned within the vasculature.
Figure 5B:
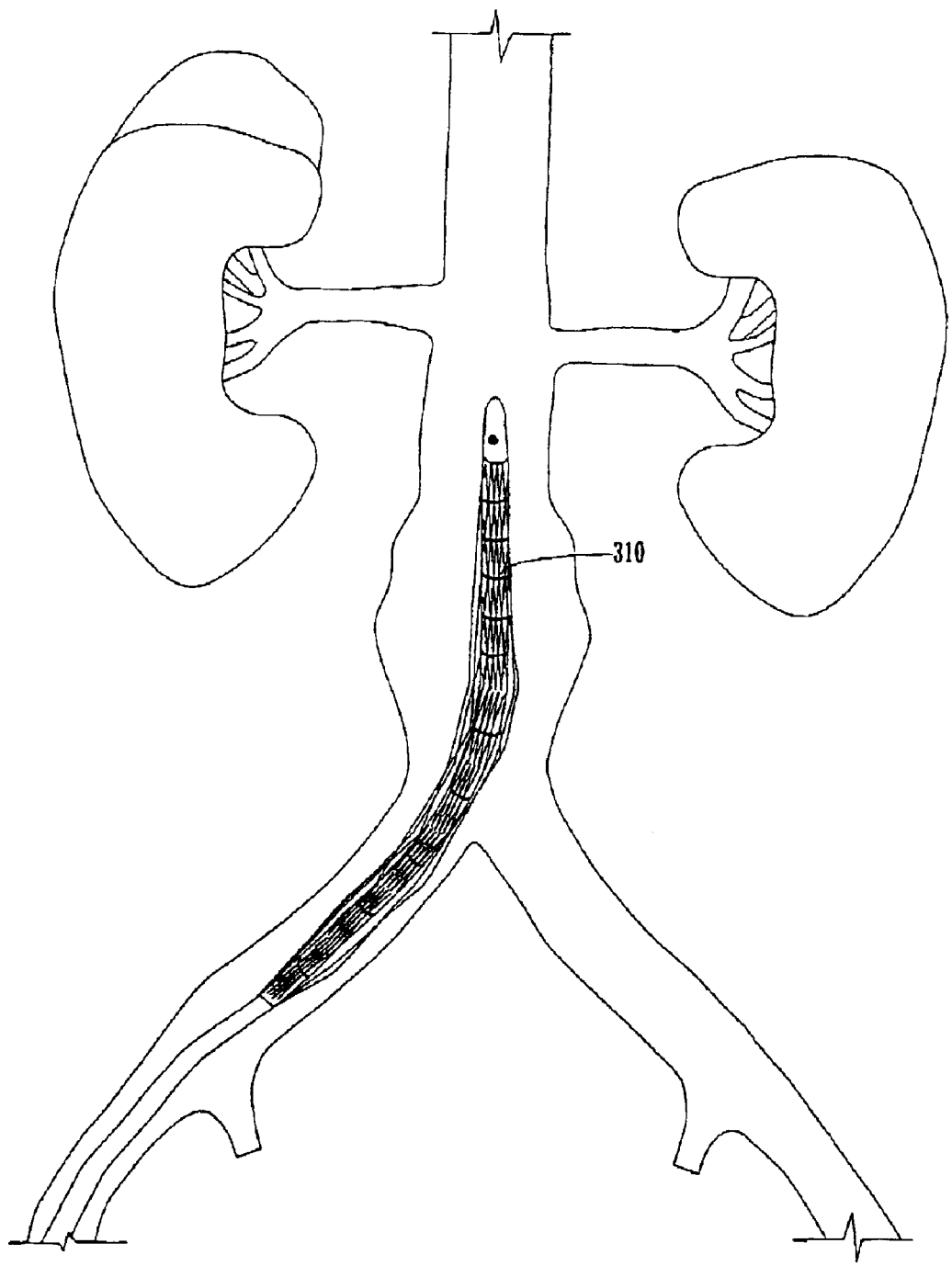
FIG. 5B is a side elevational partial cross sectional view of the endoluminal prosthesis and delivery system of FIG. 4A as the graft cover is retracted.
Figure 5C:
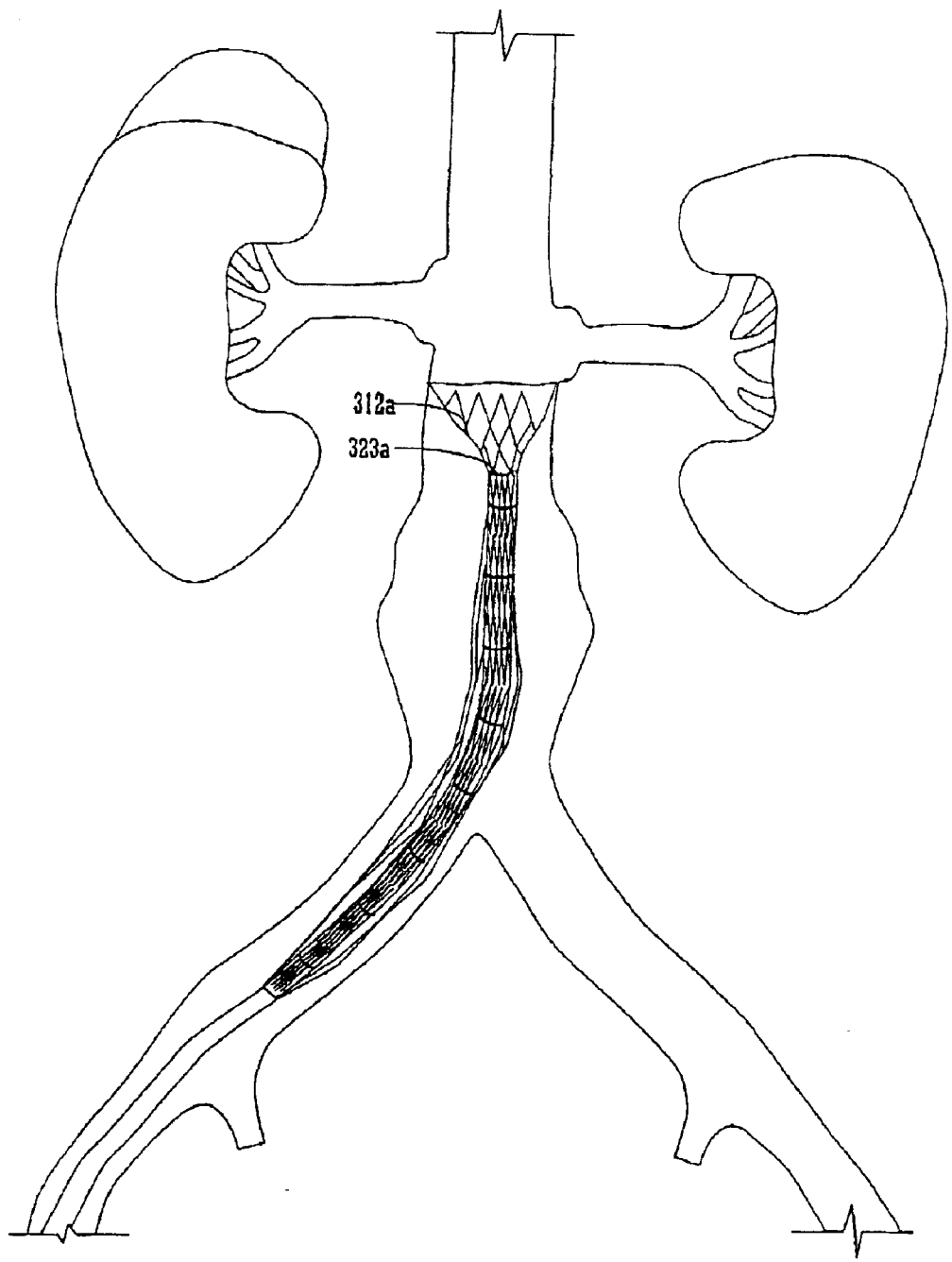
FIG. 5C is a side elevational partial cross-section of the endoluminal prosthesis and delivery system of FIG. 4A as the prosthesis is positioned and deployment is initiated.

Referring to FIGS. 5A–5D, the prosthesis 312 of FIGS. 4A–B are illustrated in a deployment procedure in which the annular support members 312 are sequentially deployed. To deploy the prosthesis 310, the main body portion 316 of the prosthesis is loaded into a catheter 326 in a collapsed configuration. Annular members 312 are held in a radially compressed configuration by the restraining mechanisms 323 to facilitate delivery of the prosthesis 310. A thin flexible sheath or cover 327 is placed over the prosthesis 310 to prevent it from damaging or catching on the luminal wall as it is delivered to the aneurysm site. Restraining of the prosthesis 310 by the cover 327 is minimal so that when it is retracted, the prosthesis 310 remains in the collapsed configuration. The main body portion 316 is delivered in a compressed state via the catheter 326 through a surgically accessed femoral artery, to the desired deployment site. (FIG. 5A) When the distal end of the catheter 326 is located at the deployment site, the cover 327 is retracted (FIG. 5B). A first annular support member 312a is deployed by actuating release of a first restraining mechanism 323a, for example, by pulling on a first actuating thread 324a and untying the release mechanism 323a. The annular member 312a is expanded while the other annular members 312 remain in the compressed configuration. (FIG. 5C) At this point in time the configuration of the prosthesis 310 with respect to the aorta may be checked and repositioned if necessary before further deploying the prosthesis 310. The other annular members 312 are deployed sequentially by first releasing the restraining mechanism 323b and then the subsequent restraining mechanisms, to expand into the deployed position illustrated in FIG. 5D.

Subsequently, using a second catheter, the contralateral iliac extension limb (not shown) also similarly restrained, may be separately deployed through a surgically accessed femoral artery after placement of the main body portion 316 in a manner similar to that described above with respect to FIGS. 5A–5D.

Figure 6A:
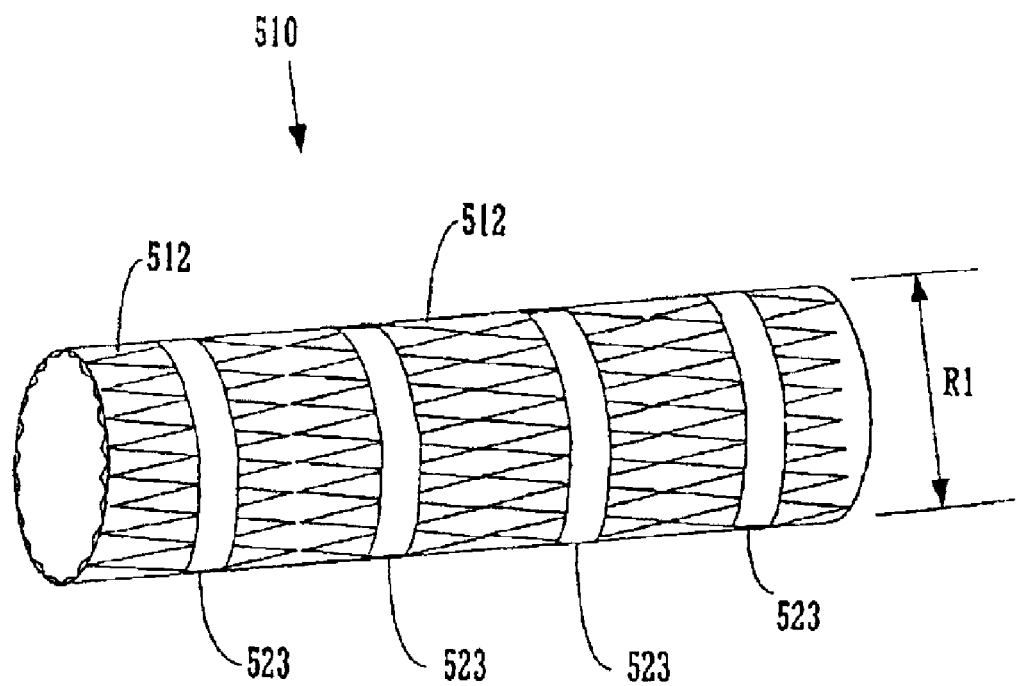
FIG. 6A is a side elevational view of another embodiment of an endoluminal prosthesis and delivery system according to the invention in a first, constrained configuration.
Figure 6B:
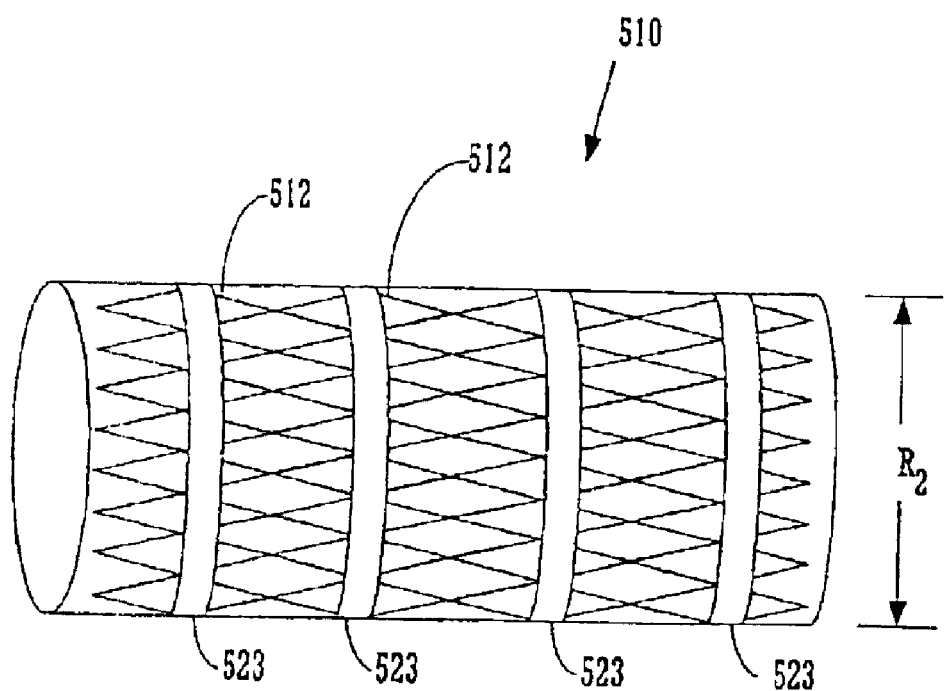
FIG. 6B is a side elevational view of the endoluminal prosthesis of FIG. 6A in a second, open configuration.

Referring now to FIGS. 6A–6B, another embodiment according to the invention is illustrated. According to this embodiment, the prosthesis 510 comprises a tubular graft 515 and annular support structures 512 attached to the tubular graft 515. The prosthesis 510 may be a single lumen stent or a bifurcated stent. The annular support structures 512 are constrained by bands of material or expansile members 523 place around each of the annular support members 512. The expansile members 523 comprise bands of a material such as a partially oriented yarn, ePTFE (expandable polytetrafluoroethylene), Teflon, or other low yield material, i.e., having a low yield point beyond which the material permanently plastically deforms. When compressed, the prosthesis 510 has a first radius R1 (FIG. 6A). The prosthesis 510 is loaded on a balloon catheter and placed at the deployment site, the balloon catheter is inflated to provide a radial force that expands the expansile members 523. The prosthesis 510 is expanded to have a second radius R2 larger than the first radius R1 (FIG. 6B). One material may be selected to have viscoelastic behavior that constrains the annular members at one temperature, e.g. at about room temperature, and deforms elastically at another temperature, e.g. at about body temperature. Suitable materials for the expansile members or bands of material 523 may include woven fibers and yarns, thermal plastics, natural materials such as cotton or silk, polyester, nylon, olefin, polypropylene, polyethylene, bioabsorbable plastics, Teflon, PTFE, ePTFE, FEP, or other fluoropolymers. An alternative to expansile members may be members or coatings formed of a sealing gel, hydrogel or the like, that may be released upon radial expansion and/or by dissolving or absorption by the body. Examples of such materials may include, for example, surgical sealants or adhesives used to close wounds, fibrin glue, collagen based materials or other bioabsorbable materials.

Figure 7:
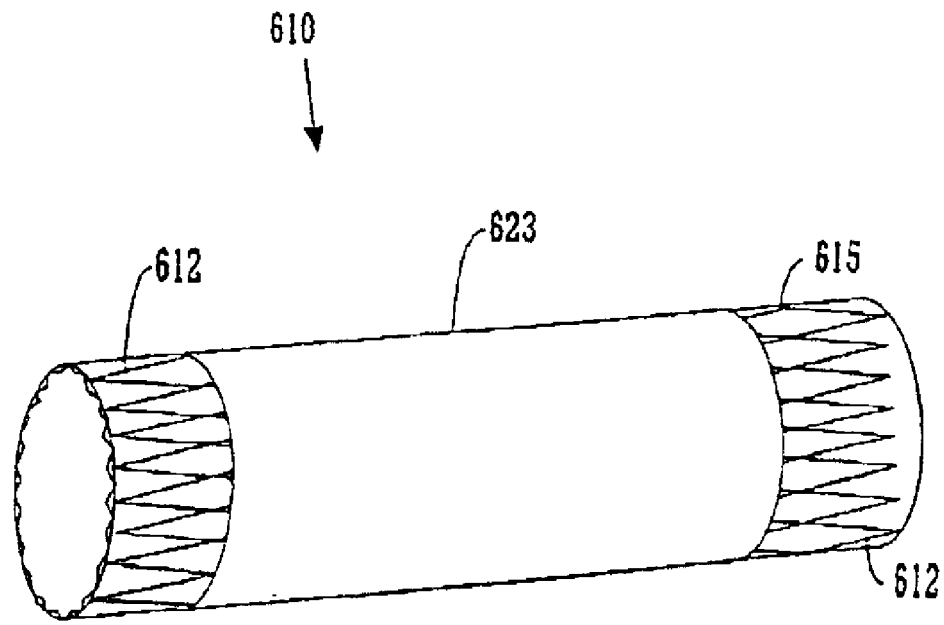
FIG. 7 illustrates a side elevational view of another embodiment of an endoluminal prosthesis and delivery system according to the invention in a first, constrained configuration.

FIG. 7 illustrates another embodiment according to the present invention. The prosthesis 610 comprises a tubular graft 615 and annular support structures 612 attached to the tubular graft 615. The annular support structures 612 are constrained in a compressed configuration by a band, material, or an expansile sheath 623 placed around the tubular graft 615. The band, material, or expansile sheath 623 comprises a band of a material such as described above with respect to FIGS. 6A and 6B. When the compressed prosthesis 610 is loaded on a balloon catheter and placed at the deployment site, the balloon catheter is inflated to provide a radial force that expands the band, material, or expansile sheath 623 to engage the wall of the aorta. Alternatively or in addition, the band material or expansile sheath may dissolve or be absorbed by the body.

Figure 5D:
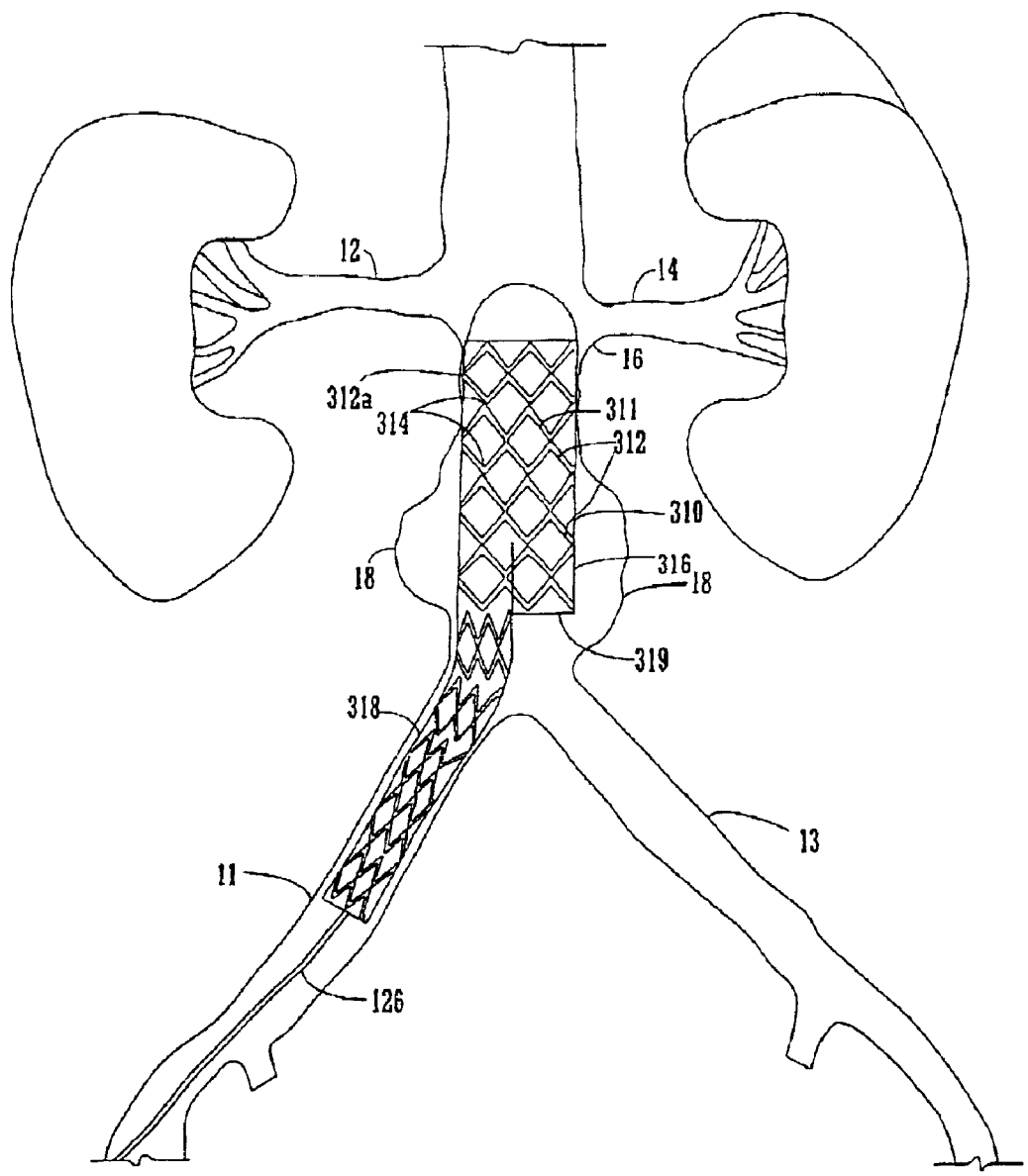
FIG. 5D is a side elevational partial cross-section of the endoluminal prosthesis and delivery system of FIG. 4A the prosthesis is fully deployed.
Figure 8:
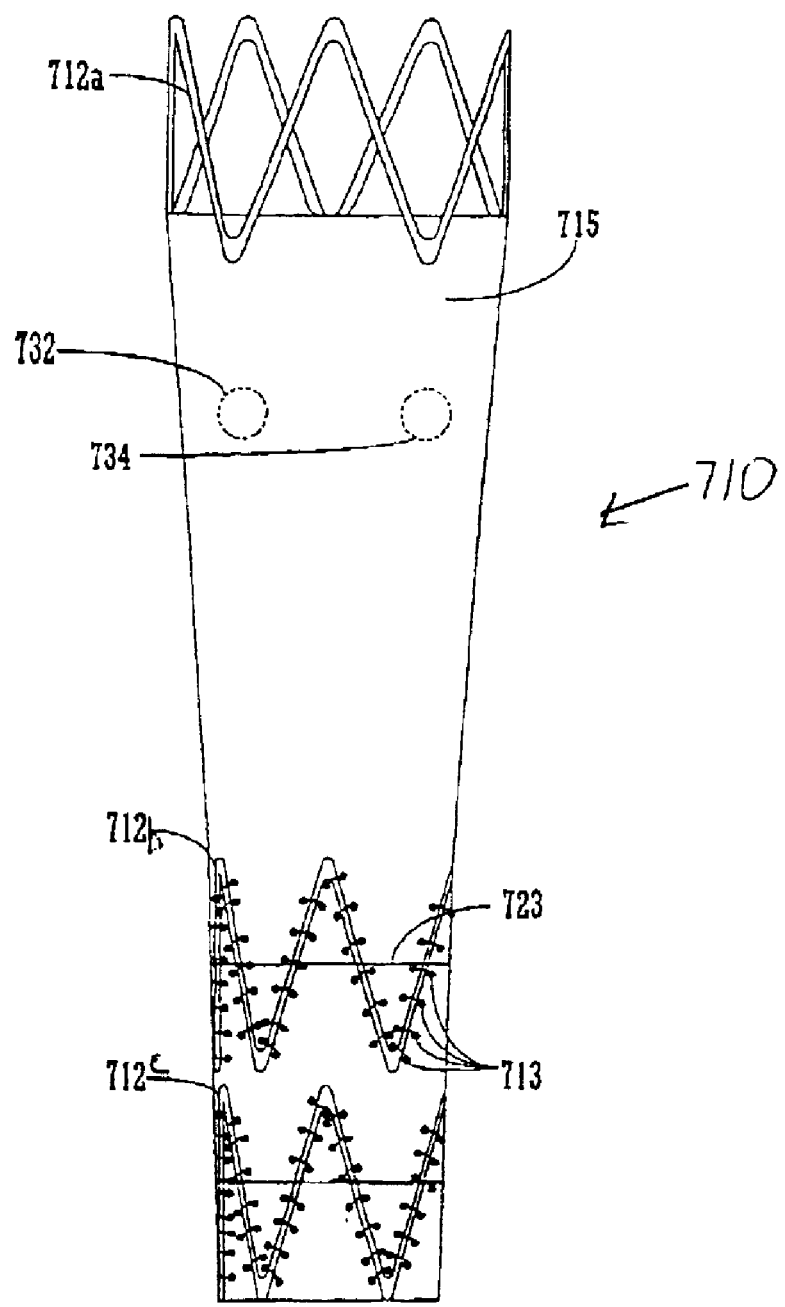
FIG. 8 illustrates a side elevational view of another embodiment of an endoluminal prosthesis according to the invention.

FIG. 8 illustrates another embodiment according to the invention. A prosthesis 710 comprises a tubular graft 715 and annular support structures 712 attached to the tubular graft 715 with sutures 713. Sutures 723 constrain the support structures 712 in a similar manner as described above with reference to support structures 212 and sutures 223 in FIG. 3B. The proximal most support structure 712a is fixed to the graft by sutures (not shown) only at the bottom end. The proximal support structure 712a is not constrained by a suture 223 but when loaded on a catheter may be otherwise constrained for independent deployment. Openings 732, 734 are formed in the graft for positioning adjacent renal arteries 12, 14 in a manner, for example, that is described with reference to U.S. Pat. No. 5,984,955 to Wisselink, the content of which is incorporated herein by reference. As noted above, the proximal most support structure 712a is held in a compressed configuration prior to deployment (not shown). The other support members may be covered by a protective sheath during delivery. In use, the prosthesis 710 is loaded onto a balloon catheter with a cap on its distal end restraining the proximal most support member 712a. The prosthesis 710 is then positioned within the vasculature so that the openings 732, 734 are near the renal arteries 12, 14 (FIG. 5D). The physician may elect not to first deploy the more distal support members 712b, 712c by expanding a balloon until the alignment of the openings 732, 734 is acceptable. The position of the openings 732, 734 may then be adjusted. The physician may then subsequently release the proximal most support member 712a. These steps may be switched in any order that the physician sees fit for implanting the prosthesis 710. Once the prosthesis 710 is positioned and deployed, stents or grafts may also be placed through the openings 732, 734 into the renal arteries, for example, as described in U.S. Pat. No. 5,984,955 to Wisselink.

Although this detailed description sets forth particular embodiments according to the invention, various other vascular grafts, endoluminal prostheses, and delivery systems are contemplated, especially those in which a self-expanding prosthesis is held by a restraining mechanism prior to deployment.

While the invention has been described with reference to particular embodiments, it will be understood to one skilled in the art that variations and modifications may be made in form and detail without departing from the spirit and scope of the invention.

I claim:

1. An endoluminal prosthesis comprising:
   a tubular graft comprising a graft material forming a lumen for the flow of body fluid therethrough;
   at least one self-expanding annular support member coupled to the graft material, wherein each of the support members has a first radially compressed configuration and a second expanded configuration in which the tubular graft is supported by the at least one annular support member; and
   at least one restraining member configured to restrain at least a portion of the at least one self-expanding annular support member in the first radially compressed configuration, wherein the at least one restraining member has a selected radial release force and is constructed to release the at least one self-expanding annular support member to permit it to expand to the second configuration upon application of an outward radial force at least as great as the selected radial release force of the restraining member.

2. The endoluminal prosthesis of claim 1 wherein the at least one restraining member encircles the at least a portion of the at least one annular support member.

3. The endoluminal prosthesis of claim 2 wherein the at least one restraining member comprises a suture.

4. The endoluminal prosthesis of claim 2 wherein the at least one restraining member comprises a wire.

5. The endoluminal prosthesis of claim 2
   wherein the at least one restraining member comprises a band of material.

6. The endoluminal prosthesis of claim 5 wherein the band of material comprises a viscoelastic material.

7. The endoluminal prosthesis of claim 5 wherein the band of material comprises a woven material.

8. The endoluminal prosthesis of claim 5 wherein the band of material comprises a sealing gel.

9. The endoluminal prosthesis of claim 5 wherein the band of material comprises a sheath restraining a plurality of the annular support members.

10. The endoluminal prosthesis of claim 1
    wherein the at least one restraining member comprises a failure fiber constraining at least a portion of the at least one annular member.

11. The endoluminal prosthesis of claim 10 wherein the failure fiber comprises a material that breaks upon the application of a sufficient radially expanding force to the at least one annular support member.

12. The endoluminal prosthesis of claim 1
    wherein the at least one annular support member comprises a plurality of diamond structures having middle portions connecting an adjacent diamond structure, wherein the at least one restraining member is coupled to a plurality of the middle portions to compress at least one of the diamond structures.

13. The endoluminal prosthesis of claim 12 wherein the at least one restraining member comprises a clip.

14. The endoluminal prosthesis of claim 12 wherein the at least one annular support member comprises a plurality of struts connecting adjacent curved portions, wherein the at least one restraining member is coupled to a plurality of the struts to compress at least one annular support member.

15. The endoluminal prosthesis of claim 1 wherein the at least one restraining member comprises a plurality of restraining members.

16. The endoluminal prosthesis of claim 15 wherein each of the plurality of restraining members encircle a portion of the at least one self expanding annular support members.

17. The endoluminal prosthesis of claim 1 wherein the restraining member is constructed of a material having a selected configuration, wherein the selected radial release force comprises a force at which the material in the selected configuration fails thereby releasing the restraining member from restraining the at least one annular support member in the first configuration.

18. An endoluminal prosthesis comprising:
    a tubular graft comprising a graft material forming a lumen for the flow of body fluid therethrough;
    a plurality of self-expanding annular support members coupled to the graft material, wherein each of the support members has a first radially compressed configuration and a second expanded configuration; and
    a plurality of restraining members, each of the plurality of restraining members configured to restrain a corresponding one of the plurality of annular support members in the first radially compressed configuration wherein each of the plurality of restraining members is individually actuatable to release a restraining member from restraining a corresponding one of the plurality of annular support members to allow the corresponding one of the plurality of annular support members to expand to the second expanded configuration.

19. The endoluminal prosthesis of claim 18 wherein each of the restraining members is individually actuatable to release the annular support members in a sequence.

20. The endoluminal prosthesis of claim 18 wherein each of the restraining members comprises a suture encircling an annular structure.

21. An endoluminal prosthesis comprising:
    a tubular graft means forming a lumen for the flow of body fluid therethrough;
    a plurality of self-expanding annular support means coupled to the graft means, wherein each of the plurality of self-expanding support means has a first radially compressed configuration and a second expanded configuration; and
    a plurality of corresponding restraining means, each of the corresponding restraining means for restraining a corresponding one of the plurality of annular support means in the first radially compressed configuration and for releasing the plurality of annular support means in a sequence to allow the plurality of annular support means to expand in the sequence to the second expanded configuration.

22. An endoluminal prosthesis delivery system comprising:
   a delivery catheter comprising an elongate member having an expandable member located on a distal portion of the elongate member wherein the expandable member has an unexpanded configuration and an expanded configuration; and
   an endoluminal prosthesis comprising:
      a tubular graft comprising a graft material forming a lumen for the flow of body fluid therethrough;
      at least one self-expanding annular support member coupled to the graft material, wherein the at least one self-expanding annular support member has a first radially compressed configuration and a second expanded annular configuration; and
      at least one restraining member configured to restrain at least a portion of the at least one annular support member in the first radially compressed configuration, wherein the at least one restraining member has a selected radial release force and is constructed to release the at least one self-expanding annular support member to permit it to expand to the second expanded annular configuration, upon application of an outward radial force at least as great as the selected radial release force of the restraining member;
   wherein the endoluminal prosthesis is located around the expandable member in the unexpanded configuration with the at least one self-expanding annular support member in the first radially compressed configuration,
   wherein the expandable member is configured to apply an outward radial force at least as great as the selected radial release force of the restraining member to release the at least one restraining member from restraining the at least a portion of the at least one annular support member in the first radially compressed configuration to permit the at least one annular support member to expand to the second expanded annular configuration.

23. The endoluminal prosthesis delivery system of claim 22 wherein the expandable member comprises a balloon configured to expand to the expanded configuration upon inflation of the balloon.

24. The endoluminal prosthesis delivery system of claim 22 wherein the at least one restraining member is constructed of a material having a selected configuration, the selected radial release force comprises a force at which the material in the selected configuration fails thereby releasing the restraining member from restraining the at least one annular support member in the first configuration.

25. The endoluminal prosthesis delivery system of claim 22 wherein the at least one restraining member encircles the at least a portion of the at least one annular support member.

26. The endoluminal prosthesis delivery system of claim 25 wherein the at least one restraining member comprises a suture.

27. The endoluminal prosthesis delivery system of claim 25 wherein the at least one restraining member comprises a wire.

28. The endoluminal prosthesis delivery system of claim 25 wherein the at least one restraining member comprises a band of material.

29. The endoluminal prosthesis delivery system of claim 28 wherein the band of material comprises a viscoelastic material.

30. The endoluminal prosthesis delivery system of claim 28 wherein the band of material comprises a woven material.

31. The endoluminal prosthesis delivery system of claim 28 wherein the band of material is expandable to a yield point where the material plastically deforms upon expansion of the expanding member.

32. The endoluminal prosthesis delivery system of claim 28 wherein the band of material comprises a sealing gel.

33. The endoluminal prosthesis delivery system of claim 28 wherein the band of material comprises a sheath restraining a plurality of the annular support members.

34. The endoluminal prosthesis delivery system of claim 22 wherein the at least one restraining member comprises a failure fiber constraining the at least a portion of the at least one annular member.

35. The endoluminal prosthesis delivery system of claim 34 wherein the failure fiber comprises a material that breaks upon the application of a sufficient radially expanding force to the at least one annular support member.

36. The endoluminal prosthesis delivery system of claim 22 wherein the at least one annular support member comprises a plurality of diamond structures having middle portions connecting an adjacent diamond structure, wherein the at least one restraining member is coupled to a plurality of the middle portions to compress at least one of the diamond structures.

37. The endoluminal prosthesis delivery system of claim 36 wherein the at least one restraining member comprises a clip.

38. The endoluminal prosthesis delivery system of claim 22 wherein the at least one annular support member comprises a plurality of struts connecting adjacent curved portions, wherein the at least one restraining member is coupled to a plurality of the struts to compress at least one annular support member.

39. The endoluminal prosthesis delivery system of claim 22 wherein the at least one restraining member comprises a plurality of restraining members.

40. The endoluminal prosthesis delivery system of claim 39 wherein each of the plurality of restraining members encircle a portion of the at least one self expanding annular support members.

41. A method of deploying an endoluminal prosthesis delivery system comprising:
   an endoluminal prosthesis means comprising:
      a tubular graft means forming a lumen for the flow of body fluid therethrough;
      a self-expanding annular support means coupled to the graft means, wherein the support means has a first radially compressed configuration and a second expanded annular configuration; and
      a restraining means for restraining the annular support means in the first radially compressed configuration and for releasing the annular support means upon application of a radial force to allow the annular support means to expand to the second expanded configuration; and
   a delivery catheter means comprising a balloon means for releasing the restraining means, the balloon means located on a distal portion of the catheter means wherein the balloon means has an unexpanded configuration and an expanded configuration,
   wherein the endoluminal prosthesis means is located around the balloon means in the unexpanded configuration with the self expanding annular support means in the first radially compressed configuration, and
   wherein the balloon means is configured to expand to the expanded configuration upon inflation of the balloon means to release the restraining means from restraining the annular support means in the first radially compressed configuration to permit the annular support means to expand to the second expanded configuration.

42. A method of deploying an endoluminal prosthesis comprising the steps of:

providing a delivery catheter comprising an elongate member having a balloon located on a distal portion of the elongate member wherein the balloon has an unexpanded configuration and an expanded configuration; and providing an endoluminal prosthesis comprising:
- a tubular graft comprising a graft material forming a lumen for the flow of body fluid therethrough;
- at least one self-expanding annular support member coupled to the graft material, wherein the at least one annular support member has a first radially compressed configuration and a second expanded configuration; and
- at least one restraining member configured to restrain the at least one annular support member in the first radially compressed configuration;

wherein the endoluminal prosthesis is located around the balloon the unexpanded configuration with the at least one self expanding annular support member in the first radially compressed configuration;

after locating a delivery catheter at a site for deployment of the endoluminal prosthesis, expanding the balloon to the expanded configuration by inflating the balloon to release the at least one restraining member from restraining the at least one annular support member in the first radially compressed configuration, and permitting the at least one annular support member to expand to the second expanded configuration.

* * * * *